US011883118B2

(12) United States Patent
Samadani et al.

(10) Patent No.: US 11,883,118 B2
(45) Date of Patent: Jan. 30, 2024

(54) USING AUGMENTED REALITY IN SURGICAL NAVIGATION

(71) Applicants: United States Government as Represented by the Department of Veterans Affairs, Washington, DC (US); HENNEPIN HEALTHCARE SYSTEMS, INC., Minneapolis, MN (US)

(72) Inventors: Uzma Samadani, Minneapolis, MN (US); Abdullah Bin Zahid, Minneapolis, MN (US); David P. Darrow, Minneapolis, MN (US)

(73) Assignees: United States Government As Represented By The Department Of Veterans Affairs, Washington, DC (US); Hennepin Healthcare Systems, Inc., Minneapolis, MN (US)

( * ) Notice: Subject to any disclaimer, the term of this patent is extended or adjusted under 35 U.S.C. 154(b) by 0 days.

(21) Appl. No.: 17/984,651

(22) Filed: Nov. 10, 2022

(65) Prior Publication Data

US 2023/0073041 A1    Mar. 9, 2023

Related U.S. Application Data

(63) Continuation of application No. 16/605,989, filed as application No. PCT/US2018/028838 on Apr. 23, 2018, now abandoned.
(Continued)

(51) Int. Cl.
*A61B 5/05*    (2021.01)
*A61B 34/20*    (2016.01)
(Continued)

(52) U.S. Cl.
CPC ............... *A61B 34/20* (2016.02); *G06F 17/16* (2013.01); *G06T 19/006* (2013.01); *G16H 30/40* (2018.01); *G16H 40/63* (2018.01)

(58) Field of Classification Search
CPC ........ A61B 34/20; G16H 30/40; G16H 40/63; G06F 17/16; G06T 19/006
See application file for complete search history.

(56) References Cited

U.S. PATENT DOCUMENTS

2004/0111183 A1*  6/2004  Sutherland ............. A61B 34/76
                                                                700/245
2007/0198022 A1*  8/2007  Lang ................... A61B 17/1666
                                                                606/88
(Continued)

FOREIGN PATENT DOCUMENTS

CA        3072257      10/2019
EP        18726581.4   11/2019
(Continued)

OTHER PUBLICATIONS

Kuroda, Tomohiro et al. (2010) "Application of AR in medical fields: interaction between medical practice information and clinical site" Joho-shori, vol. 51, No. 4, pp. 398-402, 542 (2010), Information Processing Society of Japan.

*Primary Examiner* — Joel F Brutus
(74) *Attorney, Agent, or Firm* — Ballard Spahr LLP (57) ABSTRACT

A surgical navigation system may include a processor and a display. The processor may receive a patient image and sensor data captured by a sensor, receive a medical image, generate a hologram of the medical image, perform coregistration between the patient image and the hologram, superimpose the hologram on the patient image, and display the superimposed image. Coregistration may be performed manually via a user interaction, or automatically based on one or more fiducials in the medical image and sensor data (Continued)

related to the fiducials. The system may monitor a change in the environment and update the display correspondingly. For example, the system may monitor a movement of a body of the patient, monitor the size of an organ of the patient as the organ is being under operation, or a movement of the surgical instrument. The sensor may be an augmented reality (AR) sensor in an AR device.

29 Claims, 5 Drawing Sheets

Related U.S. Application Data (60) Provisional application No. 62/488,452, filed on Apr. 21, 2017.

(51) Int. Cl.
*G16H 30/40* (2018.01)
*G16H 40/63* (2018.01)
*G06F 17/16* (2006.01)
*G06T 19/00* (2011.01)

(56) References Cited

U.S. PATENT DOCUMENTS

| | | | |
|---|---|---|---|
| 2014/0081659 A1* | 3/2014 | Nawana | A61B 5/4833 705/3 |
| 2014/0095993 A1 | 4/2014 | Kawahara | |
| 2014/0235995 A1 | 8/2014 | Owen | |
| 2016/0063707 A1 | 3/2016 | Masumoto | |
| 2016/0191887 A1 | 6/2016 | Casas | |
| 2016/0267659 A1* | 9/2016 | Vasey | A61B 90/36 |
| 2016/0324580 A1* | 11/2016 | Esterberg | A61B 34/10 |
| 2017/0116729 A1* | 4/2017 | Stolka | G06V 20/52 |

FOREIGN PATENT DOCUMENTS

| | | |
|---|---|---|
| JP | 2014-131552 | 7/2014 |
| JP | 2016-158911 | 9/2016 |
| JP | 2020-507511 | 10/2019 |
| WO | WO 2012/088535 | 6/2012 |
| WO | PCT/US2018/028838 | 4/2018 |

\* cited by examiner

USING AUGMENTED REALITY IN SURGICAL NAVIGATION

CROSS-REFERENCE TO RELATED APPLICATIONS

This application is a continuation of U.S. patent application Ser. No. 16/605,989, filed on Oct. 17, 2019, which is a national stage filing under 35 U.S.C. 371 of International Application No. PCT/US2018/028838, filed on Apr. 23, 2018, which claims benefit of priority pursuant to 35 U.S.C. § 119(e) of U.S. provisional patent application No. 62/488,452, filed Apr. 21, 2017. Each of the above-identified applications is hereby incorporated by reference herein in its entirety.

FIELD OF THE DISCLOSURE

The present disclosure relates generally to surgical navigation, and examples of using augmented reality (AR) during medical procedures are disclosed herein.

BACKGROUND

A major challenge during a surgery is to differentiate between diseased tissues and healthy tissue. Traditional procedures in a surgery require that a surgeon visually inspect and grossly determine whether an involved tissue is different from a healthy one. Current neuronavigation systems take an image of a patient's body part prior to the surgery, display the image on a screen during a surgery, and correlate a surgeon's instrument to a location of the image in real-time. However, neuronagivation systems require a surgeon to look away from the patient during the operation. As such, the existing systems present technical problems.

SUMMARY

A system using augmented reality ("AR") for surgical navigation may receive medical image of interest, such as from medical resonance imaging ("MRI"), computed tomography ("CT"), ultrasound ("US"), microscopes, or any other devices. The system may use a sensor, e.g., an AR sensor, to detect changes in the environment, render holograms representing the medical image, and place holograms relative to the environment, e.g., a patient's body.

Various different devices can be used as the sensor for AR-neuronavigation system. The examples of sensors include ultrasound, a camera (video, SLR, infrared etc.), or any other 3D scanning device. Multiple such devices of one type or multiple types might be used to increase the accuracy during procedures, surgery or other medical interventions. The placement of the images relative to the patient's body can be achieved using coregistration. The coregistration uses information from image of interest and the environment and then the system may use this mutual information to place the image of interest relative to the environment. The system may display the structures of interest from the image as a hologram in the real world, or display images and objects of interest on to a screen.

The coregistration can be accomplished in multiple ways. For example, the system may use the holographic rendering of patient's skin visible on medical image of interest and correlate that with the actual skin sensed by the AR system. The system may also allow a user to adjust the holographic rendering of the skin relative to the patient's body manually. Additional fiducials can be placed on patient's body, the fiducials may be visible on the medical image or can be sensed by the AR sensors. These fiducials can then guide the placement of the hologram relative to the patient. The system may also use 3D scanning as an AR sensor, and the resulting information can be correlated with the image of interest, which allows the accurate placement of the holograms relative to the patient body.

Additionally, and/or alternatively, the system may display a magnified view of the areas of interest by gathering high definition images and or combining multiple modalities, and creating magnified holograms. This may facilitate precise surgery. For example, the system may provide a binocular view in cases where it is otherwise impossible with other means, e.g. endoscopic, or laparoscopic surgery. Different objects, organs, lesions, or other areas of interest can be shaded or colored differently to further help easier identification.

The information from the sensors can be used to perform the coregistration as described above globally or locally. For example, in addition to global coregistration, an ultrasound probe can be inserted into the body to provide better and more precise local information. This local information can be used as is or can also be overlaid on to the previously existing global coregistration.

In some examples, the system may track fiducials that are placed on a patient's face, for example, and update the coregistration according to the displacement and or rotation of the fiducials. This allows a surgery to be performed without requiring the patient to have the patient's body part, e.g., the head, immobilized by placing it in pins (Mayfield). Similar results can also be achieved by using facial recognition methods instead of using fiducials, where natural facial features serve as fiducials.

The system provided herein can be used as intra operative imaging device. For example, the system may detect changes in the surgical environment in real time, and update the representation of the real world. This updated representation of the real world can be overlaid onto an MRI, and can help assess, for example, the amount of surgical progress, such as the amount of tumor that has been removed.

In some examples, the system may update the map and structure of objects in its surroundings at regular, desired, or custom intervals. For example, in surgery, a nerve is moved to a new location due to manipulation, and the system may detect the movement of the nerve and re-arrange the holographic representation beyond the initial medical image to reflect the updated location of the nerve.

This rearrangement can be further projected onto an initial medical image, and the initial medical image can be updated to reflect the current situation. Hence, as one non-limiting example, a new MRI will be created reflecting current anatomy, using information from devices being used as AR sensors without requiring patient to have another MRI.

The system may also detect changes in the internal body organs. For example, during neurosurgery, the brain can become edematous. The system may detect a change in the size of the brain, for example, and correlate the changed size of the brain to the previously received medical image. Hence, brain edema can be quantified. The system may also detect blood loss during surgery. Similarly, image processing and updates in object shapes can help inform surgeons and other medical staff about real time cardiac output and lung function during cardiac surgery. The examples used hereinabove, which include the brain, blood, heart and lung, have been provided as representative examples and do not limit the scope of the disclosure. For example, the system described herein may also apply to other body organs.

In some scenarios, the system may detect the hands of surgical or medical personnel, as well as any instruments used in surgery, via one or more AR sensors, such as 3D scanners. The hand(s) and/or instruments can be then mapped and displayed on to the MRI image, or on the holograms. This is advantageous for many reasons. For example, it can eliminate or reduce the need for special probes. In order to enhance the sensitivity of instruments or personnel hands to the 3D scanning device being used, they may be coated with special materials to allow easier mapping. As a non-limiting example, a surgeon's hands can be made more sensitive by coating the gloves with any material that increases sensitivity. Special pointers with easier to detect materials built into them can also be used to allow surgeons to point to a structure on patient, which will then map the pointer onto the image or hologram.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION

Figure 1:
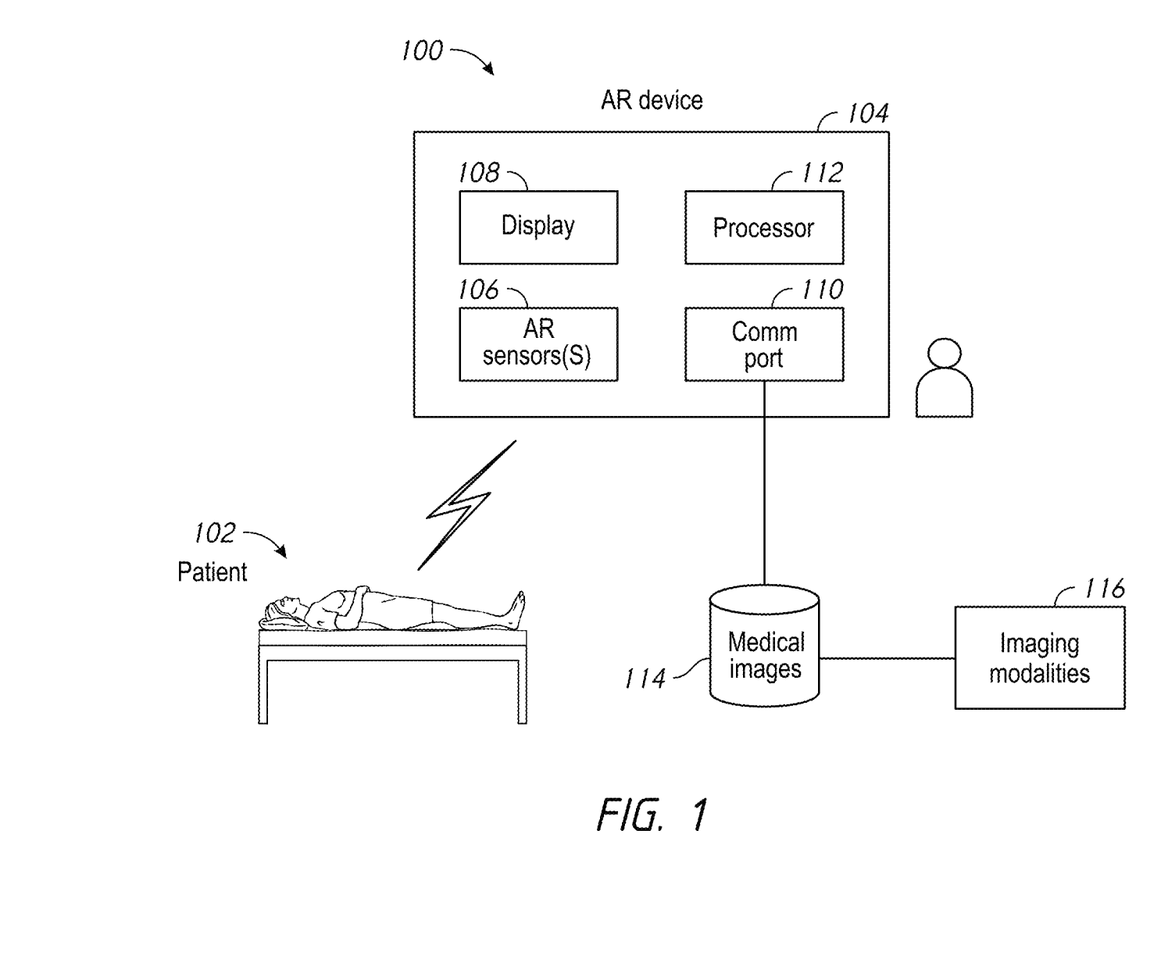
FIG. 1 illustrates a surgical navigation system in accordance with examples described herein.

In FIG. 1, a surgical system 100 may include an augmented reality (AR) device 104. The AR device 104 may include one or more AR sensors 106, a display 108, a communication port 110, and a processor 112. The AR sensor 106 is a device or a combination of devices that may record and detect changes in the environment, e.g., a surgery or procedure room 102 having a patient. These devices may include cameras (e.g. infrared, SLR, etc.), fiducials placed at known places, ultrasound probes, or any other device that is capable of three-dimensional (3D) scanning, to capture information and images in the environment. The AR sensor may also be an AR sensing device. The display 108 may display images captured from the AR sensor(s) or other sensors. Display 108 may be capable of rendering holograms. For example, the AR device 104 may include a goggle, in which the rendering of holograms can be done in real world or on a lens. Holograms can also be displayed as masks on top of images on a screen. Processor 112 may execute programming instructions to perform certain functions. For example, the programming instructions, when executed, may cause the processor to superimpose holograms relative to the real world constructed from the AR sensor(s) 106 and make them appear to be in a certain relationship to real world objects, such as a body, e.g., the head of a patient.

System 100 may also include one or more imaging modalities 116 that are configured to capture medical images 114. The imaging modalities may include, for example, MRI, CT scan, ultrasound, a microscope, or any other device. The medical images can be prerecorded or can be continuously obtained in real time. The medical images may include a static image or a sequence of images over time (e.g. functional MRI).

In some scenarios, the programming instructions for the processor 112 may be configured to coregister the medical image of interest to the information, such as a patient image, from the AR sensor, to provide a spatial mapping between the medical image and the patient image. The processor may perform the coregistration automatically by correlating one or more features of the medical image to the sensor data from the AR sensor. Alternatively, the processor may perform the coregistration in a manual process based on user interactions. Examples of coregistration will be further described in this document.

Figure 4A:
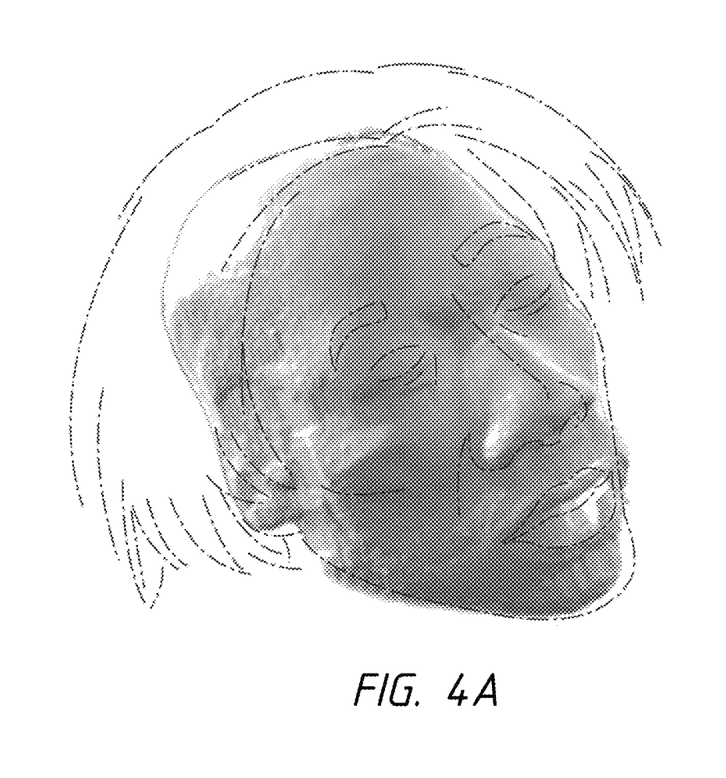
FIGS. 4A-4B illustrate the overlay of the skin of a patient's head and the brain over a patient image in accordance to some examples described herein.
Figure 4B:
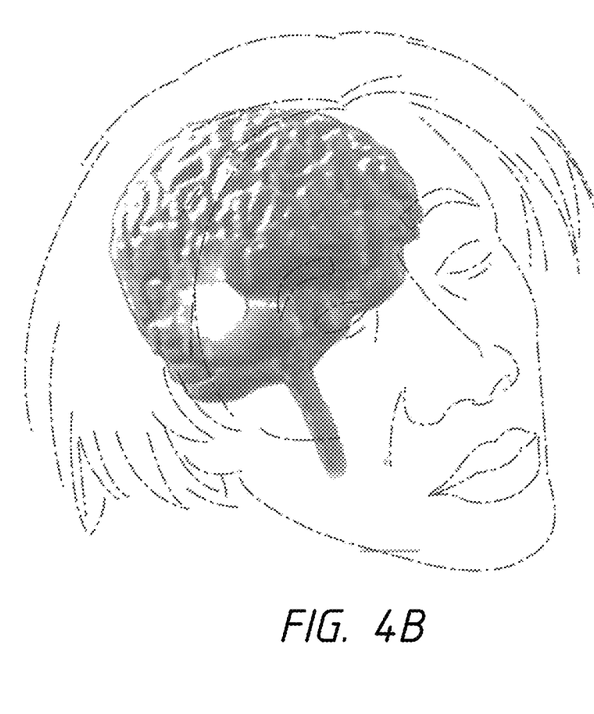

Once the medical image and the patient image are coregistered, the system may superimpose a representation of the medical image onto the patient image. For example, the representation of the medical image may be a hologram. The representation may also be the medical image itself, or a 3D model constructed from one or more medical images, such as CT images. The system may display the superimposed medical image and the patient image altogether in the display 108. This display will facilitate a view of the medical image in the context of a real-time environment. As one non-limiting example, the medical image may be the CT image of a head, and the system may construct a hologram of a patient's brain and superimpose the hologram onto a real-time image that includes a patient's head. An example is shown in FIG. 4B.

Returning to FIG. 1, in some scenarios, coregistration may not be needed if a specific relationship between real world objects and a representation of the medical image is not needed. For example, in teaching or surgical planning, images do not need to be overlaid exactly on to the patient's head. In some scenarios, when a magnified view of objects is desired (e.g. during surgery), coregistration may not be needed either.

In some scenarios, the sensors of the AR device may also capture medical images in the surgical AR system. For example, an AR sensor may be an ultrasound that can be used to obtain the images from the patient. The AR sensor images can serve multiple purposes. For example, the AR sensor images can serve as medical image of interest. The AR sensor images may also deliver the information for the AR device for spatial mapping. In some non-limiting scenarios, the AR sensor may also capture data related to the patient image. For example, the AR sensor data may include faces and vertices that describe a two-dimensional (2D) surface in 3D space, or other data pertinent to the other fiducials on the patient's body part or system.

Figure 2:
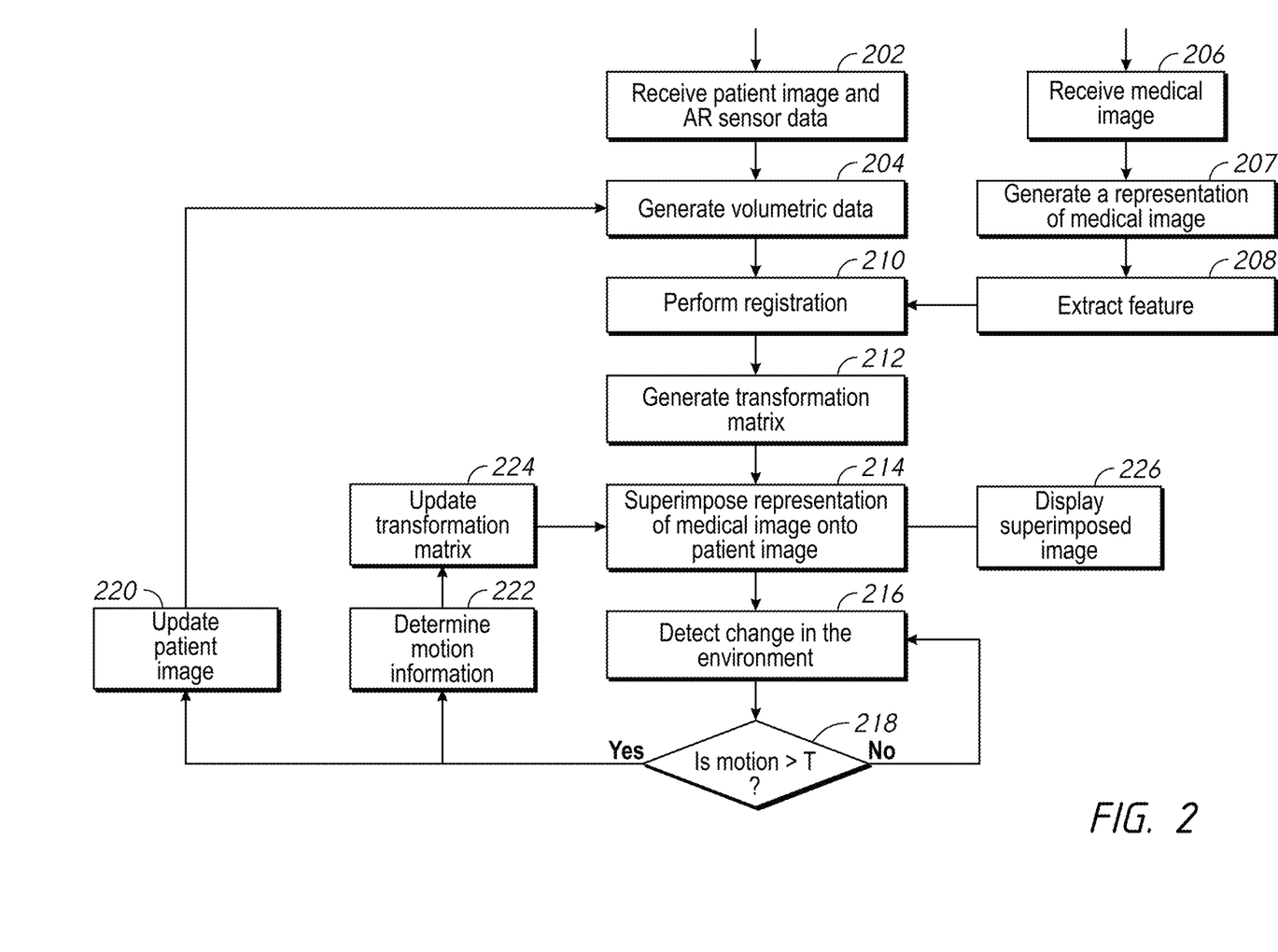
FIG. 2 illustrates examples of processes for using augmented reality in surgical navigation in accordance with examples described herein.

Various methods may be implemented in above described system. In FIG. 2, examples of processes for superimposing a representation of a medical image onto a patient image are further described. In some scenarios, a method may start with receiving AR sensor data 202 from one or more AR sensors. AR sensor data may include patient image and/or sensor data related to the patient image. The method may also include receiving medical image 206 from one or more imaging modalities, and performing coregistration 210 to generate a spatial mapping between the medical image and the patient image. In preparing for registration, the method may generate volumetric data 204 based on the data from the AR sensor, for example, faces and vertices that describe a two-dimensional (2D) surface in 3D space. The methods may convert a 2D surface into a 3D matrix. For example, William E. Lorensen, Harvey E. Cline: *Marching Cubes: A high resolution* 3*D surface construction algorithm. In: Computer Graphics*, Vol. 21, Nr. 4, July 1987, describes a marching cubes algorithm. Other algorithms may also be available.

In some non-limiting scenarios, the method may further include generating a representation of the medical image 207, such as a hologram. For example, the method may generate a hologram of the skin (or any external visible surface) from the CT scan. The skin or any external visible surface of a patient may be suitable as fiducials for coregistration. In some scenarios, the method may include selecting all the voxels in the CT scan with an attenuation value of approximately −150 Hu. This will yield a mask with all the voxels other than those pertaining to patient's head excluded. Optionally, this mask may have holes in it. For example, the nasogastric structures, nasal sinuses, external ear canals and other structures that normally contain air may have the voxels corresponding to air in them excluded as well. Optionally, the method may fill these holes to yield an improved reconstruction of the head.

In some scenarios, the method may fill the holes by doing a 3D operation on the image. Alternatively, and/or additionally, the method may fill the holes by doing a 2D operation on each slice of the image. Methods for filling holes are known. For example, a sample algorithm for filling holes is described in Soille, P., *Morphological Image Analysis: Principles and Applications*, Springer-Verlag, 1999, pp. 173-174. In some scenarios, the method may exclude some small areas that are not part of a patient's body, e.g., the head, by retaining the connected components of the image that exceed a threshold size. In some scenarios, the method may receive input from the user to adjust the mask.

Once the mask of fiducials has been segmented, the volumetric data can be converted into vertices and faces. Many different algorithms can be used for this process as well, one representative one is William E. Lorensen, Harvey E. Cline: *Marching Cubes: A high resolution* 3*D surface construction algorithm. In: Computer Graphics*, Vol. 21, Nr. 4, July 1987. This data can be used to create the hologram of the object.

In some scenarios, the method may also generate representations, e.g., holograms of the objects of interest other than the ones used as fiducials. As one non-limiting example, the method may generate holograms of a patient's body parts, conditions, or malformations, including but not limited to the brain, tumor(s), artery or arteries, vein(s) or hematoma. The relationship between fiducials and other objects of interest can be computed using either AR sensor or medical image. After the coregistration, the representation can be switched from fiducials view (e.g. skin view) to object of interest view (e.g. brain and hematoma view).

In some scenarios, the method may include receiving surgical incision sites and/or trajectories relative to the medical image. The system may convert the incisions and trajectories into holograms or representations of their own, and display the representations of the incisions and trajectories during the surgery when needed to guide actual incision or trajectory. In some examples, the holograms are displayed on the patient. In other examples, the rendering of holograms can be done in real world or on a lens, such as on goggles.

In some scenarios, the method may include extracting one or more features 208 from the medical image, where the features may be suitable for use as fiducials in the registration 210. For example, the medical image may include a CT head image, and the method may extract the skin (or other structure being used as fiducial). In the case of skin, this can be accomplished by the same process that was described with reference to box 207. The method may further discard other unrelated structures to allow for better coregistration. In some scenarios, block 208 may be option; whereas in other cases, block 208 may help improve the accuracy of coregistration.

With further reference to FIG. 2, coregistration (block 210) is described in detail. In performing coregistration 210, the method may need the medical image (for example, CT head image) to coregister and also the data from the AR sensor regarding the head of the patient. Existing registration algorithms may be available. For example, intensity based coregistration may be available. Feature based coregistration algorithms may also be available.

Additionally, and optionally, the method may receive spatial referencing information about both the patient image and the medical image, which make the registration process faster. In some scenarios, the spatial referencing information is important, for example, when the voxels in CT head are not isotropic, with their thickness is always greater than width and length. In AR sensor data, however, voxels are isotropic. The spatial referencing will help ease this limitation.

In some scenarios, for example, when both images come from one real world object i.e. patient's head, that was first scanned using CT scan and now is being sensed using AR device, the method may use Euclidian/rigid body registration/registration with six degrees of freedom for block 210.

The method may further generate a transformation matrix 212 which can be used in conjunction with the location of the patient's head from AR sensor data to place the hologram. While the steps in box 210 and 212 can be computational expensive, the method may be implemented in a computer that may be in communication with the AR device. For example, the computer may be external to the AR device and may be connected to the AR device using USB, Bluetooth, WiFi or other communication protocols.

In performing the coregistration 210, the method may use suitable features as fiducials, such as the skin or external surface when the AR sensor includes a camera. Alternatively, and/or additionally, when other AR sensors, e.g., ultrasound, are used, the method may select other structures, e.g. skull for coregistration. In some scenarios, in addition to using skin as a feature for automatic coregistration, the method may also place fiducials on the patient's body. For example, fiducials can be placed on the patient's body before acquiring the medical image. This way, the fiducial information in a medical image can be used in to correlate the medical image with the patient's actual head. The fiducials can also be placed after the acquisition of medical images, in which case they can be detected by the AR sensor device(s). This would facilitate the detection of a change in the environment, such as a movement of a patient's head. In some scenarios, the method may use any other method of 3D scanning to correlate medical image with the patient's body.

Figure 3:
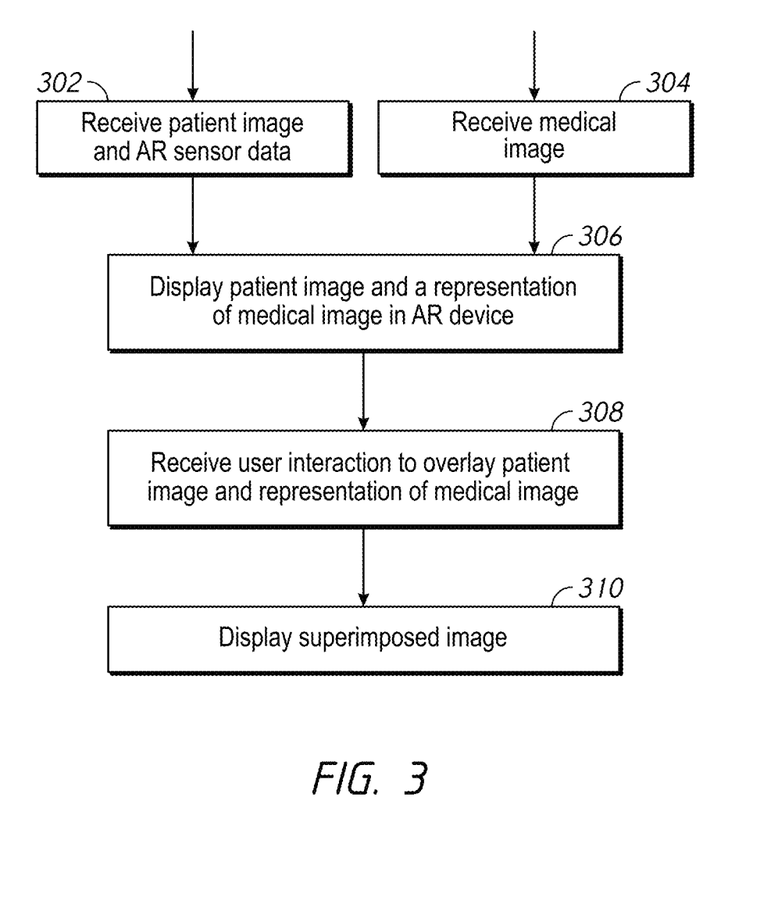
FIG. 3 illustrates an example of a process for manual coregistration in accordance with examples described herein.

With reference to FIG. 3, the registration method may include a manual process via a user interaction. For example, the method may include receiving a patient image and AR sensor data 302, receiving a medical image 304, and displaying the patient image and a representation of the medical image in the AR device 306. For example, the method may generate a hologram of the external surface or skin of the patient based on the medical image, as described early in this document. The method may render the hologram of the external surface/skin relative to the environment on the display device of the AR device (e.g. 108 in FIG. 1). The method may initialize at some point relative to the environment, then may allow the user to move and rotate the hologram along x, y or z axis and receive a user interaction to overlay the patient image and the hologram of the medical image until the user is satisfied with the overlay result. The method may display superimposed image 310 based on the user interaction.

Returning to FIG. 2, once the registration is complete, the method may superimpose the representation of the medical image onto the patient image 214 based on the transformation matrix and display the superimposed image 226 on the display of the AR device (e.g., 108 in FIG. 1). This may allow a surgeon to directly look at the medical image in the context of the real object, such as the patient's head simultaneously, while performing the surgery.

The position, size and the orientation of the hologram is determined by the values of x, y and z coordinates, rotation and scale. After initialization, the user may view the hologram and the patient's face through the AR device. User can move the hologram by changing the values for rotation, scale or location of x, y and z components. This needs to be done continuously until the user is satisfied with the overlay of the hologram on to the actual patient's skin. In this process, the data from the AR sensor regarding the shape of the head is not needed. Instead, the user is looking at the patient's head in the display while moving the hologram so that it gets overlaid on to the patient's head appropriately.

Instead of displaying a patient's skin using an AR rendering device, the method can also display on the screen or any other display modality, and this can allow the user to see the relationship between the real world patient body and the skin mask segmented earlier. This can then in turn be used to help manually coregister the two, if desired.

In FIG. 2, some or all of the devices serving as AR sensors or to obtain the medical image can be inside the patient body, for example, an endovascular catheter with ultrasound probe on its tip can be placed inside a blood vessel during the procedure and the data obtained from the probe can be both used as medial image and a way to detect a change in the environment, which will be described as below.

With further reference to FIG. 2, the method may allow a patient's body to move while the surgery is in operation. This will free the patient from being immobilized, such as constrained by any pins, e.g., Mayfield skull pin. In some scenarios, the method may detect a change in the environment 216, for example, a movement of the patient's head. The method may use data from multiple different devices, such as cameras in the AR sensor to detect the head movement. The method may also use images from multiple ultrasound probes and from multiple video cameras to register them together to increase the resolution of the final representation of the environment. In some scenarios, the method may use facial recognition to detect the movement of a patient's head during the surgery. Similarly the method may use 3D scanning, such as using an AR sensing device, to detect the changes in the environment.

In some scenarios, the method may determine whether a change in the environment, e.g., the movement of the patient's head, exceeds a threshold T 218. For example, the method may use object recognition to track a patient's head and provide the updated position and rotation of the patient's head. The tracking of an object may be done by existing methods, such as the methods provided by Vuforia library (https://library.vuforia.com/articles/Solution/How-To-Use-Object-Recognition-in-Unity). If the method determines that the change in the environment relative to the previous position has exceeded a threshold, the method may determine the motion information 222. For example, the method may determine that the movement of the patient's head has exceeded 1 mm, or the patient's head has rotated more than one degree.

Once a change in the environment is detected, e.g., a movement of the patient's head, the method may update the transformation matrix 224. For example, the method may obtain the x, y, z rotation and translation components of the transformation matrix, then adding to those components the change in value (obtained in box 222) to update the transformation matrix 224. The method may further repeat box 214 and box 226, without repeating coregistration 210. As such, the initial coregistration can be manual, such as shown in FIG. 3, without sacrificing the performance of the system.

Alternatively, and/or additionally, the method may receive an updated patient image 220 after determining that a change in the environment has occurred and/or has exceeded a threshold T 218. For example, the method may obtain the entire isosurface mesh for the external surface of the patient' head. The method may repeat boxes 204, 210, 212, 214 and 226. In other words, the method may repeat coregistration each time a change in the environment, or a change in the location of fiducials is detected.

The various embodiments in FIG. 2 use continuous updates from one or more AR sensors to detect a change in the environment, including anything being used as fiducials, e.g. the skin or external body surface of the patient, or custom fiducials placed on/in patient's body. The updated location of the fiducials can be correlated with the image of interest. Hence the representation (e.g. hologram) of the image of interest will move with the moving patient's head. This can help increase patient comfort and creating more room for surgery by eliminating the device used for immobilization.

In some scenarios, the methods described in FIG. 2 may facilitate intra operative monitoring. For example, the system may use the AR sensor to detect changes in the positioning of the normal anatomical structures. For example, during acoustic neuroma resection surgery, the identification of facial nerve (VII cranial nerve) is of key importance. The nerve can be initially located by image guidance because the anatomy matches the imaging. As drilling of the temporal bone proceeds, the nerve is no longer held in its position. Images can no longer correctly identify the nerve because the nerve is at a different location compared to when image was taken and anatomy has changed. The system may use the AR sensor to continuously detect and update the anatomy as drilling is being done. The system may detect the changes in the nerve location and move the hologram of the nerve as the nerve moves.

In some scenarios, the system may also use the updated knowledge of the nerve to update the initial CT or MRI image that was being used. Hence a CT or MRI image with updated nerve location will be available based on object tracking performed by the AR sensing device without acquiring a new MRI image.

In some scenarios, the methods described in FIG. 2 may also track the changes in the anatomy as it is being modified. For example, during an acoustic neuroma surgery, as a bone is being removed, the system may detect the removal of the bone and update the representation of the bone (whether on a display or as a hologram). This can further in turn be used to update the CT or MRI image with the appropriate portions of the bone removed. The same can be applied to tumor resection. At times, tumor appears as normal to the human eye, but is visibly different on imaging. The updated size of tumor detected by AR-sensor can be overlaid on the images and hence the clinical decision of whether to continue the removal of the tumor or not can be augmented. It should be noted that for intra operative imaging, the removal of acoustic neuroma is being presented as an example only. The system may apply to different medical procedures on different parts of a body in a similar manner.

In some scenarios, the constant monitoring from AR sensing device can also be used to quantify a change in anatomical structures. For example, if the brain is getting edematous during surgery, the AR-sensor can quantify the changed brain volume and estimate the edema. Similarly, the system may quantify the blood loss in the surgery by continuously updating representations of the environment and output the estimate of the blood loss to the user. In some or other scenarios, the system may quantify a change in heart and/or lung volumes during the cardiac and respiratory cycles and in turn measure their function.

In some scenarios, the system may use the AR sensor, for example, to track and capture a movement of a surgeon's hand(s) and instruments. The system may track the location of the surgeon's hands and instruments and overlay them to the images and holograms. This will allow the user to correlate the location of the instrument with the anatomy without using a special probe. Additionally, special probes may also be used. Optionally, the gloves or the instruments may be coated with a material that is easier for AR sensing device to detect. This can in turn, allow the representation of the instruments or hands to be overlaid on to the image.

If the AR sensor (e.g., ultrasound) is capable of detecting changes in the deeper layers of the tissue, then the system may use the AR sensor to find the location of the surgical instruments inside the tissue as well. Even though static representations of the instrument can be projected on to the images as well, at times, more flexible catheters and other instruments e.g., deep brain stimulator leads get bent while going through the brain parenchyma. The system may detect this bent inside the brain by using an ultrasound probe and superimpose it on to image, which may show to the surgeon the final path and location of the catheter or deep brain stimulator leads.

It may be appreciated that the boxes shown in FIG. 2 may have variations, and some may be optional or combined. In some scenarios, the system may generate the representation of the medical image 207, e.g., a hologram, and display the hologram without superimposing the representation onto the patient image. For example, the system may provide a magnified 3D view or a binocular 3D view based on the holograms. In some scenarios, for example, in endoscopic surgery, the camera provides a 2-D image of the surgical field, and the depth is difficult for a surgeon to appreciate on the screen. By displaying a 3D binocular view or the magnified 3D view, the system may facilitate the surgeon to better understand the environment and/or see details of the structures of the patient's body.

Other variations are described herein. In some scenarios, while camera on the endoscope/laparoscope/bronchoscope can provide the visible view, the system may include additional AR sensors (106 in FIG. 1), such as an ultrasound probe that can being used as an AR sensor on the tip of the endoscope, to provide a 3D view. This can be useful in the situations where for example blood can obscure the camera view, but in an ultrasound image, the surgeon will still be able to view the structures covered by the blood. When bleeding occurs in a surgery, the system may allow the surgeon to identify the artery responsible for the bleeding, e.g., in a hologram based on the ultrasound image, and control the bleeding by clamping that artery. This may not be possible by using a camera as the AR sensor when the camera view is obscured by the blood.

Holograms of different organs can be color coded or can be created from different materials. This difference in shading, colors, transparency or reflection may allow the user to easily differentiate between different tissue types e.g. lesion versus normal tissues versus blood.

In some scenarios, the system may perform the coregistration (e.g. box 210 in FIG. 2) for the entire body part for both the medical image and the patient image. Alternatively, and/or additionally, the method may perform a local coregistration that may be suitable for the surgical field. For example, the system may use ultrasound probes in the surgical field to create a 3D view of the field itself and the structures beneath it, for example, an artery. The method may perform a local coregistration by correlating the location of an artery in the ultrasound from an AR sensing device to the medical image from an imaging modality. This will facilitate more precise location of lesion than possible with global coregistration only.

In some scenarios, the system may also perform a local coregistration using local landmarks. These landmarks may be custom, as picked by surgeons. Local coregistration may be done in a similar manner as described above in various embodiments in FIG. 2. For example, the method may allow a user to perform a manual coregistration by moving the local hologram to be superimposed on the patient image. Any suitable anatomical features may be thought of as natural fiducials and may be used in coregistration. Local coregistration may be advantageous when tissue deformation decreases the accuracy of the projection from global coregistration.

Once the coregistration has been done, the hologram of the skin (or the external surface, the artery, or any fiducials used etc.) can be switched to the view of interest e.g. view of surgical incision site and trajectory, hematoma and or brain.

Various embodiments described herein may facilitate a number of surgical procedures. For example, FIG. 4A shows the overlay of a patient's head skin on top of patient's own actual head image. This illustrates the principal of using natural landmarks from the patient's body as fiducials. This placement can be achieved manually or automatically as described herein. Once the hologram fully and accurately covers the patient's head, the view can be switched to the object of interest, for example, the brain in FIG. 4B.

Figure 5A:
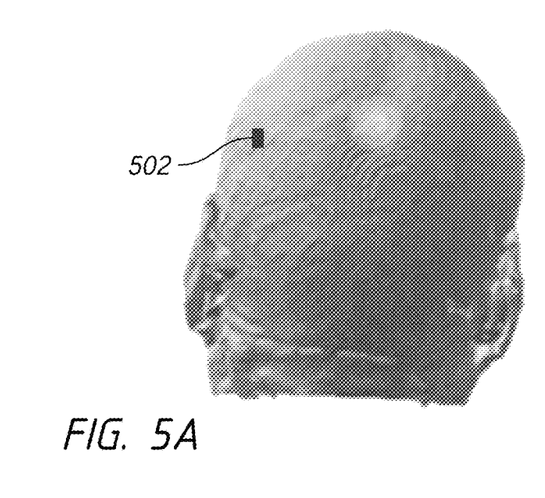
FIGS. 5A-5D illustrate an example of surgical navigation.
Figure 5B:
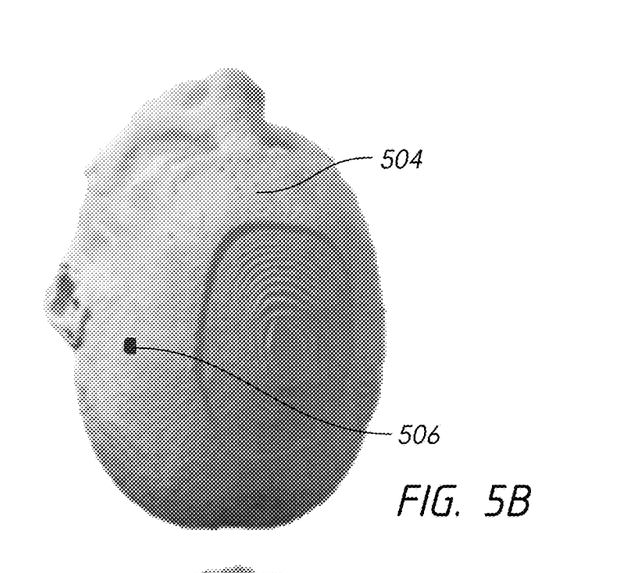
Figure 5C:
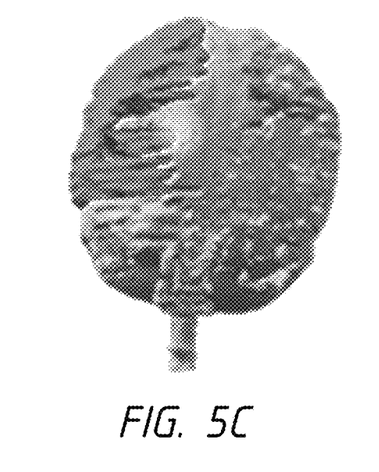
Figure 5D:
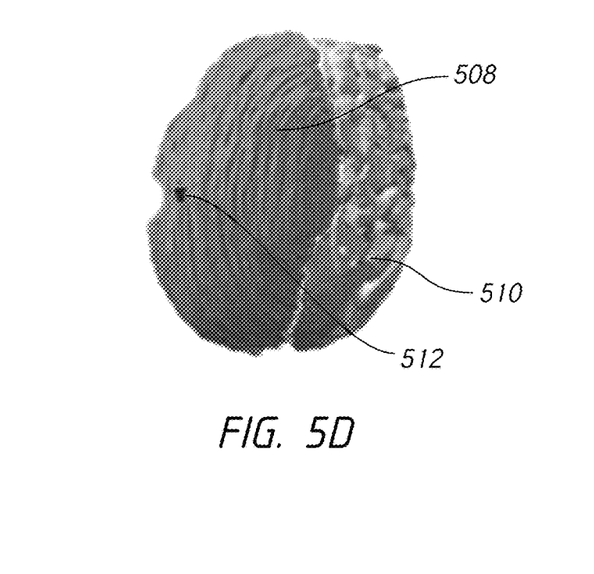

In a non-limiting example in FIGS. 5A and 5B, the hologram of a patient's head is shown. The head hologram will be moved until it accurately overlays on to the patient's actual head in all three dimmensions. FIGS. 5C and 5D show the subdural hematoma in dark and brain in light. This is the 'object of interest' in this example. The relationship between the object of interest and fiducial is known from the medical image being used. 502, 504 are different views of the patient's head external surface hologram generated using a CT image. 506, 512 are the location that surgeon decided to incise. 508 is the lesion (in this example, subdural hematoma) to be drained. 510 is the brain.

Various embodiments described herein provide solutions to the technical problems that exist in prior art systems and are advantageous in helping surgeons determine their target easily without looking away from the patient. The present disclosure also facilitates intra-operative imaging in that the system may detect changes in real-world object shapes and use information about that change to assess how much the diseased tissue, e.g., a tumor is left over. This avoids having to take the patient to the MRI, re-image and compare it to the prior MRI to determine how much residual is left over, which process is costly and time consuming.

It will be appreciated that various modifications and alterations to the described embodiments may be possible as one may be able to devise numerous systems, arrangements, and procedures which, although not explicitly shown or described herein. For example, multiple medical images may be used for coregistration. Various different exemplary embodiments can be used together with one another, as well as interchangeably therewith, as should be understood by those having ordinary skill in the art.

In an aspect of the disclosure, a system includes a processor, a display, and a computer readable non-transitory medium containing programming instructions that, when executed, will cause the processor to perform certain functions. The processor receives a patient image comprising at least a body of a patient and sensor data captured by one or more augmented reality (AR) sensors. The processor also receives a medical image, generates a representation of the medical image, and performs coregistration between the patient image and the representation of the medical image to generate a transformation matrix. The processor also superimposes the representation of the medical image onto the patient image based on the transformation matrix to form a superimposed image, and displays the superimposed image on the display.

Alternatively, and/or additionally, the system performs the coregistration manually by: displaying the patient image on the display, displaying the representation of the medical image on the display, receiving a user input to move the representation of the medical image relative to the patient image on the display, and generating the transformation matrix based on the relative location between the representation of the medical image and the patient image.

Alternatively, and/or additionally, the system perform the coregistration automatically by: extracting one or more features from the representation of the medical image, generating volumetric data based on the sensor data, and generating the transformation matrix based on the one or more features and the volumetric data.

Alternatively, and/or additionally, the one or more features include a fiducial, and the sensor data comprises information about the fiducial.

Alternatively, and/or additionally, the fiducial is a skin or an external surface of the patient image.

Alternatively, and/or additionally, the fiducial is a deep structure of the body of the patient or a marker placed on the body of the patient.

Alternatively, and/or additionally, the fiducial is an artery or septal divide between compartments of the body of the patient.

Alternatively, and/or additionally, at least one of the one or more AR sensors includes a camera, a three-dimensional (3D) scanning device, or an ultrasound device.

Alternatively, and/or additionally, the system is configured to determine a change of the body of the patient.

Alternatively, and/or additionally, the system is configured to determine a movement of the body of the patient. If the movement of the body of the patient has exceeded a threshold, the system updates the transformation matrix to generate an updated transformation matrix.

Alternatively, and/or additionally, the system updates the transformation matrix by: determining information about the movement of the body; and updating the transformation matrix based on the information about the movement of the body.

Alternatively, and/or additionally, the information about the movement of the body comprises a position change of the body from a previous position.

Alternatively, and/or additionally, the system updates the transformation matrix by: receiving an updated patient image, and performing coregistration between the updated patient image and the representation of the medical image to generate the updated transformation matrix.

Alternatively, and/or additionally, the representation of the medical image is a hologram.

Alternatively, and/or additionally, the system updates the representation of the medical image based on the information about the movement of the body.

Alternatively, and/or additionally, the body of the patient comprises at least one of a nerve, an artery, or an internal organ.

Alternatively, and/or additionally, the system determines a change of the body of the patient in size. If the change of the size of the body of the patient has exceeded a threshold, the system updates the transformation matrix to generate an updated transformation matrix.

Alternatively, and/or additionally, the system assesses a function of a heart, a lung or an internal organ of the patient, or assesses a brain edema or blood loss.

Alternatively, and/or additionally, the patient image includes a surgeon's hand or a surgical instrument in the surgeon's hand.

Alternatively, and/or additionally, the system superimpose the surgeon's hand or the surgical instrument on the medical image. Alternatively, and/or additionally, the system determines a change in a position or shape of the surgical instrument, and superimposes the surgical instrument on the medical image based on the change in the position or the shape of the surgical instrument.

Alternatively, and/or additionally, the display is a display of an AR device.

Alternatively, and/or additionally, the display is configured to render a hologram.

Alternatively, and/or additionally, the display is configured to display a 3D binocular vision.

Alternatively, and/or additionally, the display is configured to display an image of the patient image by a scaling factor, the scaling factor is equal or less than one.

In another aspect of the disclosure, a method in a surgical navigation includes: receiving a patient image comprising at least a body of a patient and sensor data captured by one or more augmented reality (AR) sensors; receiving a medical image; generating a representation of the medical image; performing coregistration between the patient image and the representation of the medical image to generate a transformation matrix; superimposing the representation of the medical image onto the patient image based on the transformation matrix to form a superimposed image; and displaying the superimposed image on the display.

Alternatively, and/or additionally, the method performs the coregistration by: extracting one or more features from the representation of the medical image; generating volumetric data based on the sensor data; and generating the transformation matrix based on the one or more features and the volumetric data.

Alternatively, and/or additionally, the method also includes determining a movement of the body of the patient. If the movement of the body of the patient has exceeded a threshold, the method updates the transformation matrix to generate an updated transformation matrix.

Alternatively, and/or additionally, the method also includes: determining a movement of a surgical instrument in the patient image; and superimposing the surgical instrument on the medical image based on the movement of the surgical instrument.

In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A system comprising:
   a processor;
   a display; and
   a computer readable non-transitory medium containing programming instructions that, when executed, will cause the processor to:
   receive a first patient image showing at least a portion of a body of a patient and sensor data captured by one or more augmented reality (AR) sensors;
   receive a medical image showing at least one anatomical structure that is not detectable by the one or more AR sensors;
   generate a representation of the medical image;
   perform coregistration between the first patient image and the representation of the medical image to generate a transformation matrix;
   superimpose the representation of the medical image onto the first patient image based on the transformation matrix to form a superimposed image;
   display the superimposed image on the display;
   receive a second patient image showing the at least a portion of the body of the patient and sensor data captured by the one or more AR sensors;
   determine a change in the at least one anatomical structure based on a change between the first patient image and the second patient image, wherein the change is caused by cutting or drilling within the body of the patient during a surgical intervention; and
   update the superimposed image on the display based on detecting the change in the at least one anatomical structure.

2. The system of claim 1, wherein the programming instructions for performing the coregistration comprise programming instructions configured to:
   display the patient image on the display;
   display the representation of the medical image on the display;
   receive a user input to move the representation of the medical image to a location relative to the patient image on the display; and
   generate the transformation matrix based on the relative location between the representation of the medical image and the patient image.

3. The system of claim 1, wherein the programming instructions for performing the coregistration comprise programming instructions configured to generate the transformation matrix automatically by:
   extracting one or more features from the representation of the medical image;
   generating volumetric data based on the sensor data; and
   generating the transformation matrix based on the one or more features and the volumetric data.

4. The system of claim 3, wherein the programming instructions that are configured to generate the transformation matrix automatically by extracting the one or more features from the representation of the medical image comprise instructions that are configured to extract one or more fiducials from the representation of the medical image, and wherein the sensor data comprises information about the fiducial.

5. The system of claim 4, wherein the instructions that are configured to extract one or more fiducials from the representation of the medical image comprise instructions that are configured to extract skin or an external surface of the patient image from the representation of the medical image.

6. The system of claim 4, wherein the instructions that are configured to extract one or more fiducials from the representation of the medical image comprise instructions that are configured to extract a deep structure of the body of the patient or a marker placed on the body of the patient from the representation of the medical image.

7. The system of claim 4, wherein the instructions that are configured to extract one or more fiducials from the representation of the medical image comprise instructions that are configured to extract an artery or septal divide between compartments of the body of the patient from the representation of the medical image.

8. The system of claim 1, wherein at least one of the one or more AR sensors includes a camera, a three-dimensional (3D) scanning device, or an ultrasound device.

9. The system of claim 1, further comprising additional programming instructions configured to determine a change of the body of the patient.

10. The system of claim 9, wherein the additional programming instructions comprise programming instructions configured to:
    determine a movement of the body of the patient; and
    update the transformation matrix to generate an updated transformation matrix if the movement of the body of the patient has exceeded a threshold.

11. The system of claim 10, wherein the programming instructions for updating the transformation matrix comprise programming instructions configured to: determine information about the movement of the body; and update the transformation matrix based on the information about the movement of the body.

12. The system of claim 11, wherein the information about the movement of the body comprises a position change of the body from a previous position.

13. The system of claim 11, further comprising additional programming instructions configured to: update the representation of the medical image based on the information about the movement of the body.

14. The system of claim 10, wherein the programming instructions for updating the transformation matrix comprise programming instructions configured to:
   receive an updated patient image; and
   perform coregistration between the updated patient image and the representation of the medical image to generate the updated transformation matrix.

15. The system of claim 9, wherein the additional programming instructions comprise programming instructions configured to:
   determine a change of the body of the patient in size; and
   update the transformation matrix to generate an updated transformation matrix if the change of the size of the body of the patient has exceeded a threshold.

16. The system of claim 9, further comprising additional programming instructions configured to: assess a function of a heart, a lung or an internal organ of the patient; or assess a brain edema or blood loss.

17. The system of claim 1, wherein the representation of the medical image is a hologram.

18. The system of claim 1, wherein the body of the patient comprises at least one of a nerve, an artery, or an internal organ.

19. The system of claim 1, wherein the patient image includes a surgeon's hand or a surgical instrument in the surgeon's hand.

20. The system of claim 1, wherein the display is a display of an AR device.

21. The system of claim 20, wherein the display is configured to render a hologram.

22. The system of claim 20, wherein the display is configured to display a 3D binocular vision.

23. The system of claim 20, wherein the display is further configured to display an image of the patient image by a scaling factor, the scaling factor is equal or less than one.

24. The system of claim 1, wherein the at least one anatomical structure comprises a tumor, wherein the surgical intervention is a tumor resection, and wherein the change in the at least one anatomical structure comprises removal of at least a portion of the tumor.

25. The system of claim 1, wherein the at least one anatomical structure comprises a nerve, wherein the surgical intervention comprises drilling of a temporal bone, and wherein the change in the at least one anatomical structure of the medical image comprises movement of the nerve.

26. A method comprising:
   receiving a patient image showing at least a portion of a body of a patient and sensor data captured by one or more augmented reality (AR) sensors;
   receiving a medical image;
   generating a representation of the medical image;
   performing coregistration between the patient image and the representation of the medical image to generate a transformation matrix;
   superimposing the representation of the medical image onto the patient image based on the transformation matrix to form a superimposed image;
   displaying the superimposed image on the display;
   receiving a second patient image showing the at least a portion of the body of the patient and sensor data captured by the one or more AR sensors;
   determining a change in the at least one anatomical structure based on a change between the first patient image and the second patient image, wherein the change is caused by cutting or drilling within the body of the patient during a surgical intervention; and
   updating the superimposed image on the display based on detecting the change in the at least one anatomical structure.

27. The method of claim 26, wherein performing the coregistration comprises:
   extracting one or more features from the representation of the medical image;
   generating volumetric data based on the sensor data; and
   generating the transformation matrix based on the one or more features and the volumetric data.

28. The method of claim 26, further comprising:
   determining a movement of the body of the patient; and
   updating the transformation matrix to generate an updated transformation matrix if the movement of the body of the patient has exceeded a threshold.

29. The method of claim 26, further comprising:
   determining a movement of a surgical instrument in the patient image; and
   superimposing the surgical instrument on the medical image based on the movement of the surgical instrument.

* * * * *